United States Patent
Earley et al.

(10) Patent No.: US 8,267,934 B2
(45) Date of Patent: Sep. 18, 2012

(54) ELECTROSURGICAL TOOL

(75) Inventors: Christopher Earley, Santa Clara, CA (US); Andrew Hamel, San Mateo, CA (US)

(73) Assignee: Stryker Corporation, Kalamazoo, MI (US)

( * ) Notice: Subject to any disclaimer, the term of this patent is extended or adjusted under 35 U.S.C. 154(b) by 2290 days.

(21) Appl. No.: 11/105,329

(22) Filed: Apr. 13, 2005

(65) Prior Publication Data

US 2006/0235377 A1 Oct. 19, 2006

(51) Int. Cl.
*A61B 18/14* (2006.01)

(52) U.S. Cl. ................. 606/50; 606/41; 604/35

(58) Field of Classification Search ............ 604/35; 606/41, 45, 48–50
See application file for complete search history.

(56) References Cited

U.S. PATENT DOCUMENTS

| | | | |
|---|---|---|---|
| 3,974,833 A | 8/1976 | Durden, III | |
| 5,290,282 A | 3/1994 | Casscells | |
| 5,324,254 A | 6/1994 | Phillips | |
| 5,395,312 A | 3/1995 | Desai | |
| 5,401,274 A | 3/1995 | Kusunoki | |
| 5,520,685 A | 5/1996 | Wojciechowicz | |
| 5,730,742 A | 3/1998 | Wojciechowicz | |
| 5,810,806 A | 9/1998 | Ritchart et al. | |
| 5,830,214 A | 11/1998 | Flom et al. | |
| 5,833,689 A | 11/1998 | Long | |
| 6,063,081 A | 5/2000 | Mulier et al. | |
| 6,102,046 A | 8/2000 | Weinstein et al. | |
| 6,156,036 A | 12/2000 | Sussman et al. | |
| 6,190,381 B1 | 2/2001 | Olsen et al. | |
| 6,214,003 B1 | 4/2001 | Morgan et al. | |
| 6,254,600 B1 | 7/2001 | Willink et al. | |
| 6,296,638 B1 | 10/2001 | Davison et al. | |
| 6,355,032 B1 | 3/2002 | Hovda et al. | |
| 6,406,476 B1 * | 6/2002 | Kirwan et al. | 606/50 |
| 6,458,126 B1 | 10/2002 | Doyle | |
| 6,482,201 B1 * | 11/2002 | Olsen et al. | 606/41 |
| 6,482,202 B1 * | 11/2002 | Goble et al. | 606/41 |
| 6,632,193 B1 | 10/2003 | Davison et al. | |
| 6,764,487 B2 * | 7/2004 | Mulier et al. | 606/41 |
| 2002/0107516 A1 * | 8/2002 | Sharkey et al. | 606/49 |
| 2003/0181904 A1 * | 9/2003 | Levine et al. | 606/45 |
| 2003/0233090 A1 * | 12/2003 | Whayne | 606/49 |
| 2005/0065510 A1 * | 3/2005 | Carmel et al. | 606/41 |
| 2005/0277916 A1 | 12/2005 | DeCesare et al. | |
| 2006/0106379 A1 * | 5/2006 | O'Brien et al. | 606/45 |

OTHER PUBLICATIONS

Stryker 90-ASD Probe discussed in paragraphs [0004] and [0005] of specification (date unknown), 2 pages.

* cited by examiner

*Primary Examiner* — Michael Peffley
(74) *Attorney, Agent, or Firm* — Flynn, Thiel, Boutell & Tanis, P.C.

(57) ABSTRACT

An electrosurgical tool for cauterizing or ablating targeted tissue, which tool includes a conductive outer shaft which defines a return or reference electrode, and a conductive inner tube disposed within the outer shaft. The inner tube defines both a suction pathway for removing fluid and/or surgical debris from the surgical site through the distal end of the tool, and a pathway for delivering electrical energy to an active electrode secured to the distal end of the suction tube.

30 Claims, 12 Drawing Sheets

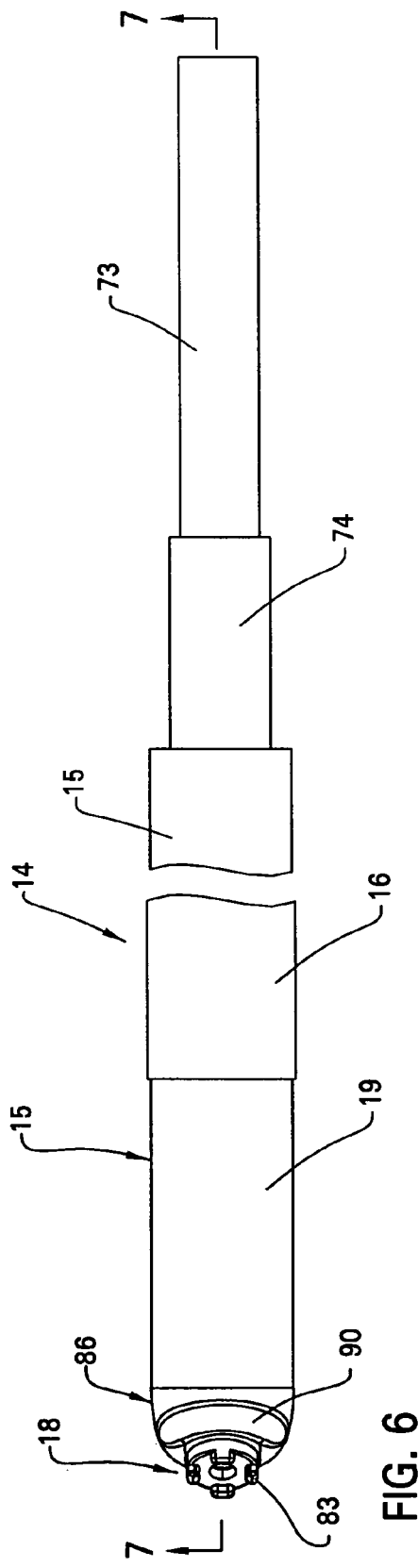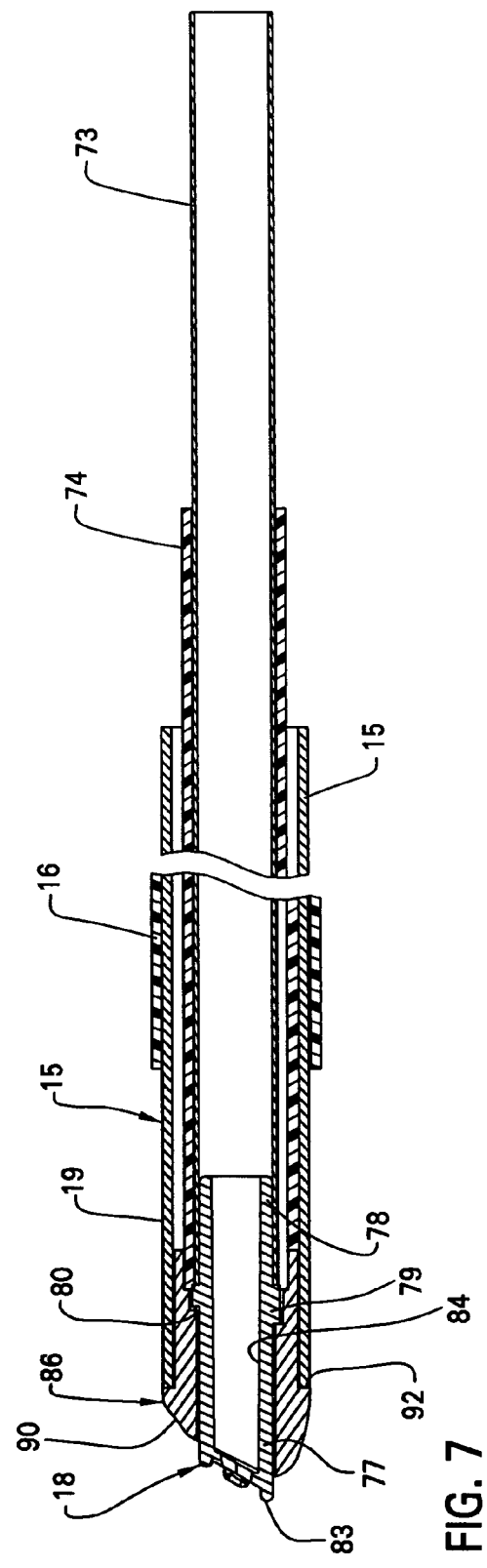
FIG. 6
FIG. 7

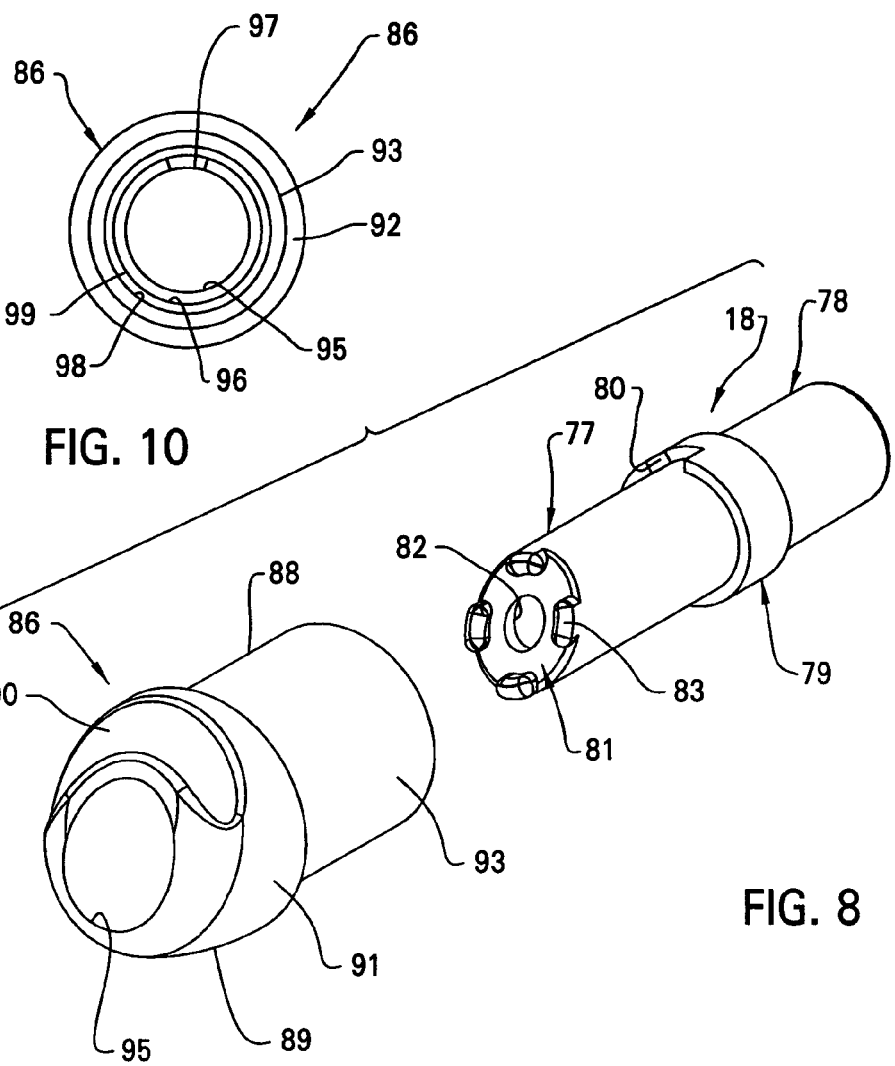
FIG. 10
FIG. 8
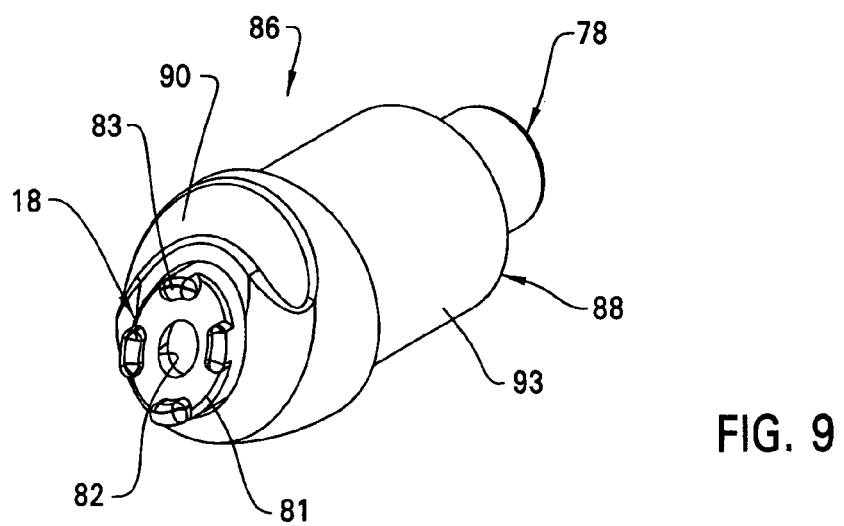
FIG. 9

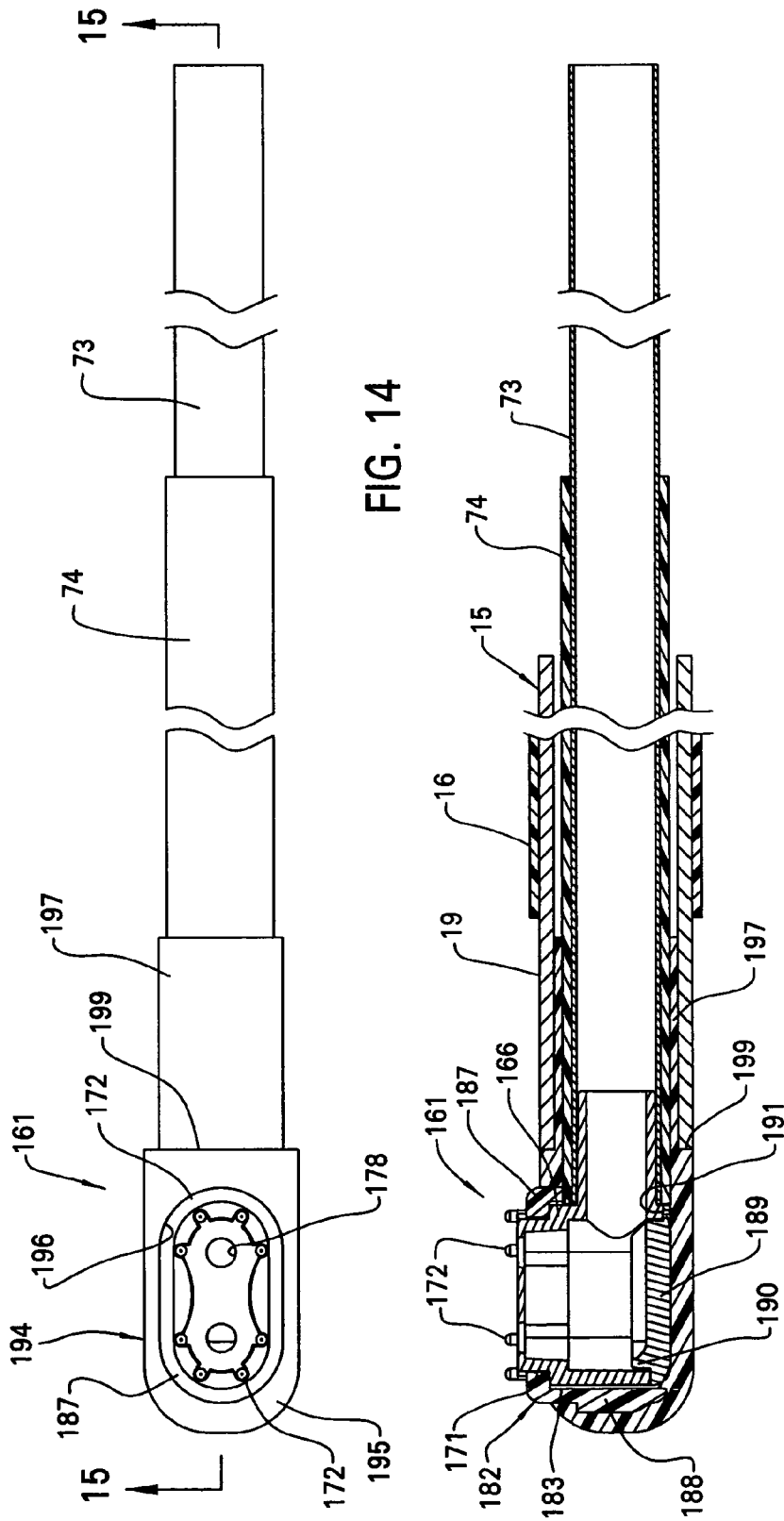

ELECTROSURGICAL TOOL

FIELD OF THE INVENTION

This invention generally relates to an electrosurgical tool for ablation and coagulation of body tissues during surgery, and specifically to an electrosurgical tool which additionally provides aspiration or suction at the tip of the tool.

BACKGROUND OF THE INVENTION

Electrosurgical tools have been available for many years which employ electrical energy to treat targeted patient tissue in various ways. For example, electrocauterization is utilized to seal off and close blood vessels during surgery to prevent blood loss. In addition, ablation is utilized to vaporize or remove tissue using electrical energy. Electrosurgical probes are typically designed to perform both of these functions, depending upon the type of power supplied thereto. Further, monopolar and bipolar electrosurgical tools have long been available, wherein monopolar tools direct electric current from an active electrode defined on the tool through the patient's body and to a return electrode, which return electrode is typically defined by a grounding pad attached to the patient. Bipolar tools, on the other hand, incorporate both an active and a return electrode directly into the tool.

Surgical procedures utilizing bipolar tools are often performed using a conductive irrigant, such as saline, for irrigation and for distending a joint, for example in orthopedic arthroscopic procedures. The conductivity of the saline solution provides a conduction pathway between the active and return electrodes of the tool. The delivery of a high-frequency current between the active and return electrodes effectively modifies tissue, and it is common for bubbles to form on the surface of the tool or probe tip which can interfere with the surgeon's view of the surgical site. This is particularly a problem when the electrosurgical tool is employed in an endoscopic surgical procedure, wherein the electrosurgical tool is inserted into the surgical site through a small opening or portal formed in the patient's body. The surgeon views the surgical site through an endoscope which is inserted into the surgical site through another portal. Thus, these bubbles are generated in the relatively small confines of the surgical site and cause significant problems for the surgeon in viewing the surgical site. Further, these bubbles are electrically and thermally insulating, and can inhibit the flow of new saline solution for rewetting the electrode. Consequently, the bubbles can cause undesirable reduction of current flow through the targeted tissue.

In order to address the undesirable bubble generation described above, some electrosurgical tools incorporate a suction feature into the tool to remove the bubbles. One type of electrosurgical tool manufactured by the Assignee hereof is capable of suction. More specifically, this tool includes an outer conductive shaft which is covered with an insulating material. The distal end of the shaft is exposed of the insulating material, and serves as a return electrode. The active electrode is disposed inside the outer shaft and is supported at the shaft tip by an insulator cap, typically constructed of ceramic. The insulator cap is mounted within the open distal end of the shaft, and defines therein two bores. The distal end of the active electrode extends through one of these bores, and a plastic suction tube extends inside and along the outer shaft and into the other bore. This arrangement thus permits a vacuum to be drawn through the tool from the distal end thereof.

Minimally invasive surgical techniques require surgical tools to be as small as possible in order to minimize trauma to the patient. As such, there is an ongoing effort to reduce the size of surgical instruments whenever possible. While the above tool works reasonably well for its intended purpose, the requirement for the outer shaft to house both a suction tube and wiring for delivering current to the active electrode presents difficulties in assembly of the tool. Further, this arrangement results in limited available space within the outer shaft, which places a limit on the diameter of a suction tube. In addition, the cap which insulates the active electrode from the return electrode is required to have multiple holes for accommodating the active electrode and suction tube, which makes it difficult to minimize the overall diameter of the insulator cap and thus the overall diameter of the tool tip.

Other conventional electrosurgical tools which are capable of suction include an elongate tubular member which defines a conduit therein for aspirating fluid and/or debris from the surgical site. This tubular member is constructed of a conductive material, and thus also functions as an energy-delivering electrode. For example, U.S. Pat. No. 5,520,685 discloses a suction coagulator defined by a tubular suction cannula covered with an insulating coating. The cannula has a distal end which is exposed of the insulating coating and defines the active electrode. An insulating sleeve is provided inside the distal end of the electrode portion of the cannula for preventing the formation of blood char. U.S. Pat. No. 3,974,833 also discloses an electrosurgical tool including a conductive suction tube which is exposed from insulating material at its distal end so as to define the active electrode. Further, U.S. Pat. No. 6,156,036 discloses an electrosurgical tool defined by inner and outer conductive tubes which are separated by an insulator. The innermost tube defines an aspiration conduit. Current is passed between the inner and outer tubes so as to boil surgical fluid located at the distal end of the tool.

The above devices advantageously incorporate a conductive tubular member which defines a conduit for fluid aspiration while simultaneously providing an electrically conductive pathway to the active electrode defined by the distal end of the tube. This structure eliminates the need for internal wiring for the electrode within the tool shaft. However, a disadvantage of the above devices is that they utilize the suction tube directly for delivery of electrical energy to the targeted tissue. That is, the electrode in the above devices is a monolithic component of the suction tube itself. Accordingly, the electrode is defined by the exposed ring-shaped distal end of the suction tube, and thus the electrode geometry is limited to the geometry of the suction tube. In an electrode having this ring-shaped geometry as defined by the exposed distal end of the suction tube, electrical flux is necessarily greatest at the periphery of the ring. However, the rate of fluid flow over this ring and into the suction passage of the suction tube can cause convective cooling at the periphery of the electrode, which can result in the inability to rapidly ablate tissue.

In order to obviate or at least minimize the disadvantages of the above devices, the instant invention is directed to an electrosurgical tool which incorporates a suction tube defining both a conduit for fluid aspiration and an electrically conductive pathway to an active electrode disposed at the distal end of the tool. The active electrode is initially formed as a separate component from the suction tube, and is joined to the distal end of the suction tube. The active electrode is preferably joined to the suction tube by a press or interference-fit, but may also be joined to the suction tube by crimping, welding, with a conductive adhesive, or by another suitable method. This structure advantageously allows more freedom in designing an electrode for optimizing energy delivery to the targeted tissue. Further, the electrode according to the invention includes a small hole which communicates with the suction conduit defined by the suction tube, which can minimize convective cooling at the periphery of the active electrode where electrical flux is greatest. The small suction hole defined in the active electrode can also help to prevent clogging downstream of the surgical site by minimizing the size of tissue fragments that enter the suction conduit.

Further, the tool according to the invention helps to resolve the spatial limitations of existing tools by eliminating the need for both a suction tube and electrode wiring to pass through the outer tool shaft and the insulator cap disposed at the distal end thereof, since a single tube serves both as a suction tube and as a conduit for delivering electrical energy to the electrode at the tip of the tool, and since only one passage must be defined through the insulator cap. As such, the internal diameter of the outer shaft can be significantly reduced, since no additional space is needed therein for electrode wiring. In addition, the diameter of the distal end of the tool can be reduced essentially to the size of the active electrode, plus the minimal ceramic thickness necessary for insulation purposes.

As an alternative to reducing the overall diameter of the tool shaft, the diameter in one embodiment can be kept identical to existing diameters, and the suction channel enlarged in order to increase flow rate. The instant invention thus maximizes the cross-sectional areas within the tool shaft by eliminating unused space therein. The concentricity of the return electrode defined by the outer shaft and the active electrode defined by the conductive suction tube allows the remainder of the available cross-sectional area to be essentially fully utilized by the suction channel, if desirable or necessary.

BRIEF DESCRIPTION OF THE DRAWINGS

FIG. 6 is an enlarged fragmentary plan view of the lumen assembly;

FIG. 7 is a cross-sectional view of the lumen assembly taken generally along line 7-7 in FIG. 6;

FIG. 8 is an enlarged, exploded perspective view of the active electrode and insulating cap;

FIG. 9 is an assembled view in perspective of the active electrode and insulating cap of FIG. 8;

FIG. 10 is an end view of the proximally-facing side of the insulating cap;

FIG. 14 is an enlarged, fragmentary plan view of a further embodiment of an active electrode arrangement;

FIG. 15 is a cross-sectional view taken generally along line 15-15 in FIG. 14;

Figure 1:
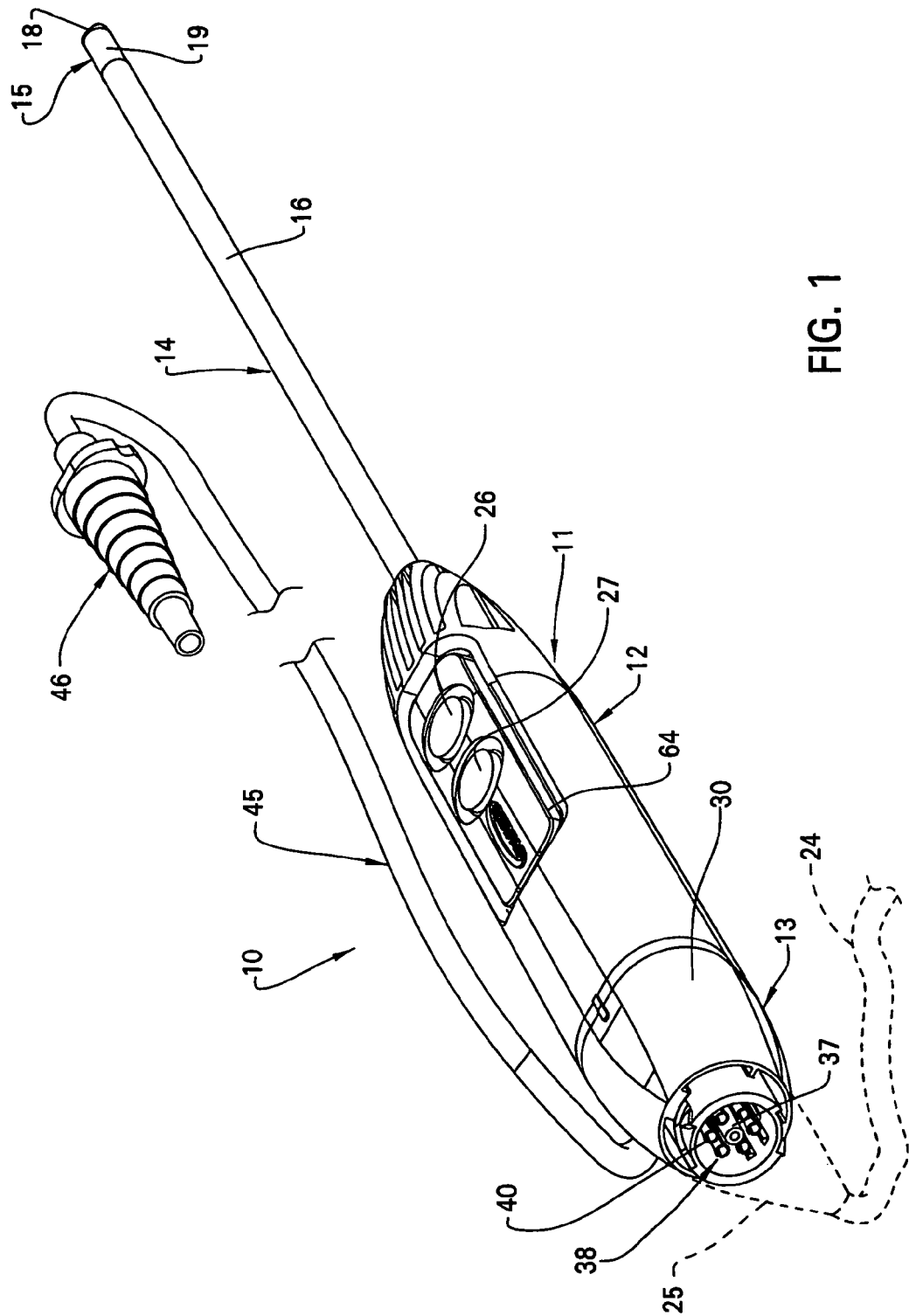
FIG. 1 is a perspective fragmentary view of the electrosurgical tool according to the invention.

Certain terminology will be used in the following description for convenience in reference only, and will not be limiting. For example, the words "upwardly", "downwardly", "rightwardly" and "leftwardly" will refer to directions in the drawings to which reference is made. The words "inwardly" and "outwardly" will refer to directions toward and away from, respectively, the geometric center of the arrangement and designated parts thereof. The words "forwardly" and "distally" will refer to the direction toward the end of the arrangement which is closest to the patient, and the words "rearwardly" and "proximally" will refer to the direction away from the end of the arrangement which is furthest from the patient. Said terminology will include the words specifically mentioned, derivatives thereof, and words of similar import.

DETAILED DESCRIPTION

Figure 2:
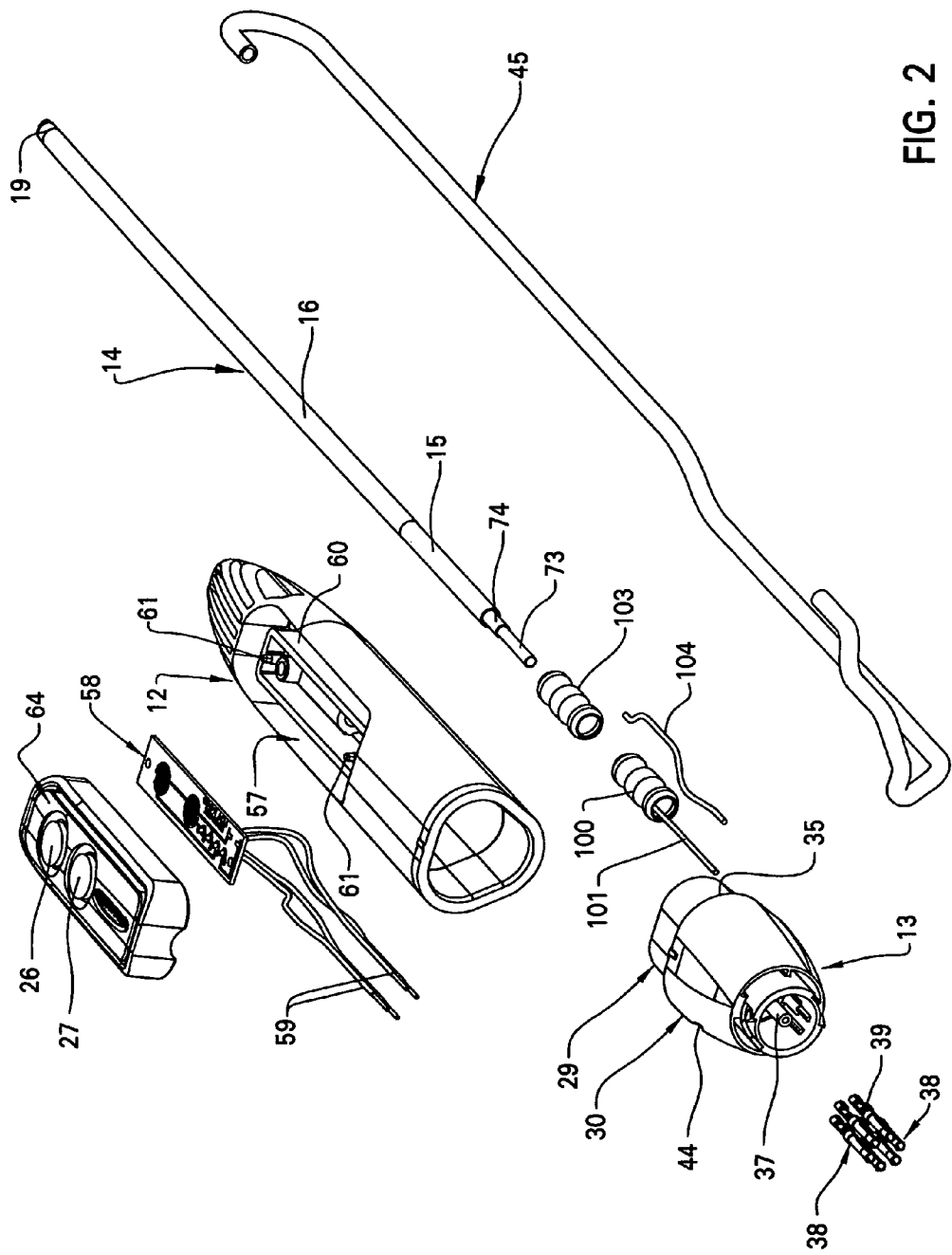
FIG. 2 is an exploded view of the tool of FIG. 1.

FIGS. 1 and 2 illustrate the electrosurgical tool 10 according to the present invention. The tool 10 includes an elongated housing 11 which serves as the handle for the tool 10. Housing 11 is defined by a generally nose-shaped, forwardly-oriented member 12 and a rear hub 13 which seats within an open proximal end of member 12. A lumen assembly 14 projects forwardly or distally from the distal end of the nose-shaped member 12. Lumen assembly 14 includes an outer tubular shaft 15 formed from conductive material, such as stainless steel, which outer shaft 15 is covered along a majority of the length thereof by an insulating material, such as a heat-shrink tube 16. The distal end of the lumen assembly 14 incorporates an electrode 18. An exposed distal end 19 of outer shaft 15 defines a return or reference electrode, while electrode 18 defines an active, energy-delivering electrode.

The current for energizing tool 10 is supplied by a control console (not shown), wherein current flows from the console to the tool 10 through a cable 24 (shown in dotted lines in FIG. 1). Cable 24 is attached to the proximal end of tool 10 by a connector 25 (also shown in dotted lines), which in the illustrated embodiment detachably and electrically connects cable 24 to tool 10. Depending upon the surgeon's commands, the control console applies either a lower power coagulating-causing signal to electrode 18, or a high power ablation-causing signal to electrode 18. The on/off actuation of the tool 10 is controlled by two normally-open switches 26 and 27 provided on member 12 of housing 11. When it is desirable to operate the tool 10 in the ablation or cutting mode, switch 26 is depressed. Switch 27 is depressed to operate the tool 10 in the coagulation mode. It will be appreciated that the tool 10 may alternatively be controlled with a foot switch, which typically includes a set of switches which are depressed to perform the same functions as the control console.

Figure 4:
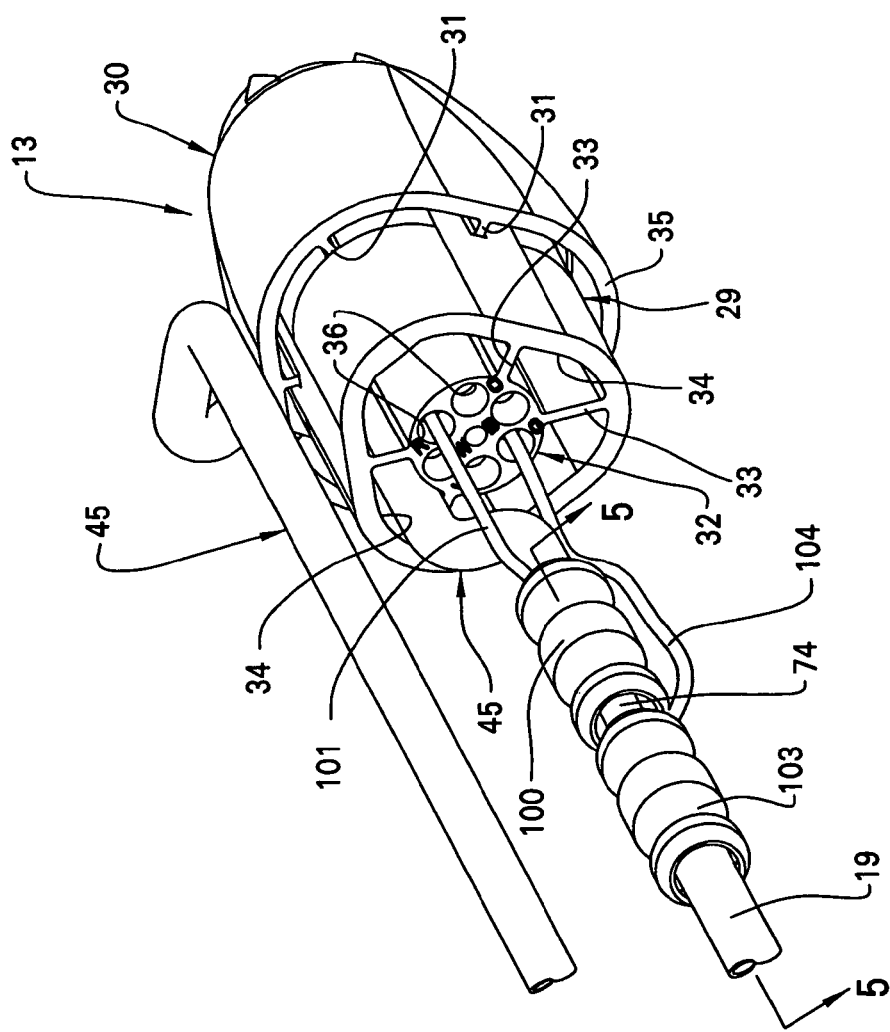
FIG. 4 is an enlarged fragmentary view of the distal end of the rear hub of the tool housing and the proximal end of the lumen assembly.

Rear hub 13 of tool 10 is similar to the tool hub disclosed in the instant Assignee's U.S. Pat. No. 6,214,003, which is hereby incorporated by reference herein in its entirety. Hub 13 is accordingly only briefly described herein. Referring to FIGS. 1, 2 and 4, rear hub 13, which in the illustrated embodiment is constructed of rigid plastic such as PVC or ABS, includes a distally projecting inner shell 29 which is sized so as to seat inside the open proximal end of nose-shaped housing member 12. An outer shell 30 is disposed about the rear end of inner shell 29, and defines the exposed portion of the hub 13. Outer shell 30 is fixed to inner shell 29 by a plurality of ribs 31 which extend between inner and outer shells 29 and 30. Hub 13 further includes a generally cylindrical core 32 which extends from the terminal distal face of inner shell 29 and rearwardly therethrough. Core 32 is secured within inner shell 29 by a plurality of supports 33 extending between the outer surface of core 32 and the inner surface of shell 29. Respective adjacent pairs of supports 30 are spaced from one another so as to define hollow spaces 34 within inner shell 29. Hollow spaces 34 extend from the terminal distal face of inner shell 29 rearwardly a short distance beyond a terminal peripheral distal edge 35 of outer shell 30.

Core 32 defines therein a plurality of through bores 36 extending through core 32 along respective axes which are generally parallel to the longitudinal axis of the tool 10. Further, a central post 37 is integrally formed with core 32 and extends rearwardly therefrom. Pin-shaped socket crimps 38 are seated within respective bores 36 of core 32. These socket crimps 38 are of a conventional construction, and one suitable such crimp is manufactured by AMP, Inc. of Harrisburg, Pa. Each socket crimp 38 has a generally sleeve-shaped distal end 39 (FIG. 2) which seats in a bore 36 of core 32, and a generally sleeve-shaped and slitted proximal end 40 which projects from core 32 (FIG. 1).

As shown in FIG. 2, outer shell 30 of hub 13 defines therein an opening 44 which opens into one of the hollow spaces 34 defined between core 32 and inner shell 29. One end of a suction tube 45 extends through this opening 44, into hollow space 34, and forwardly from inner shell 29, as best shown in FIG. 4. The opposite end of tube 45 mounts thereon an adapter 46 (FIG. 1) which is fitted to a-suction source (not shown).

Figure 3:
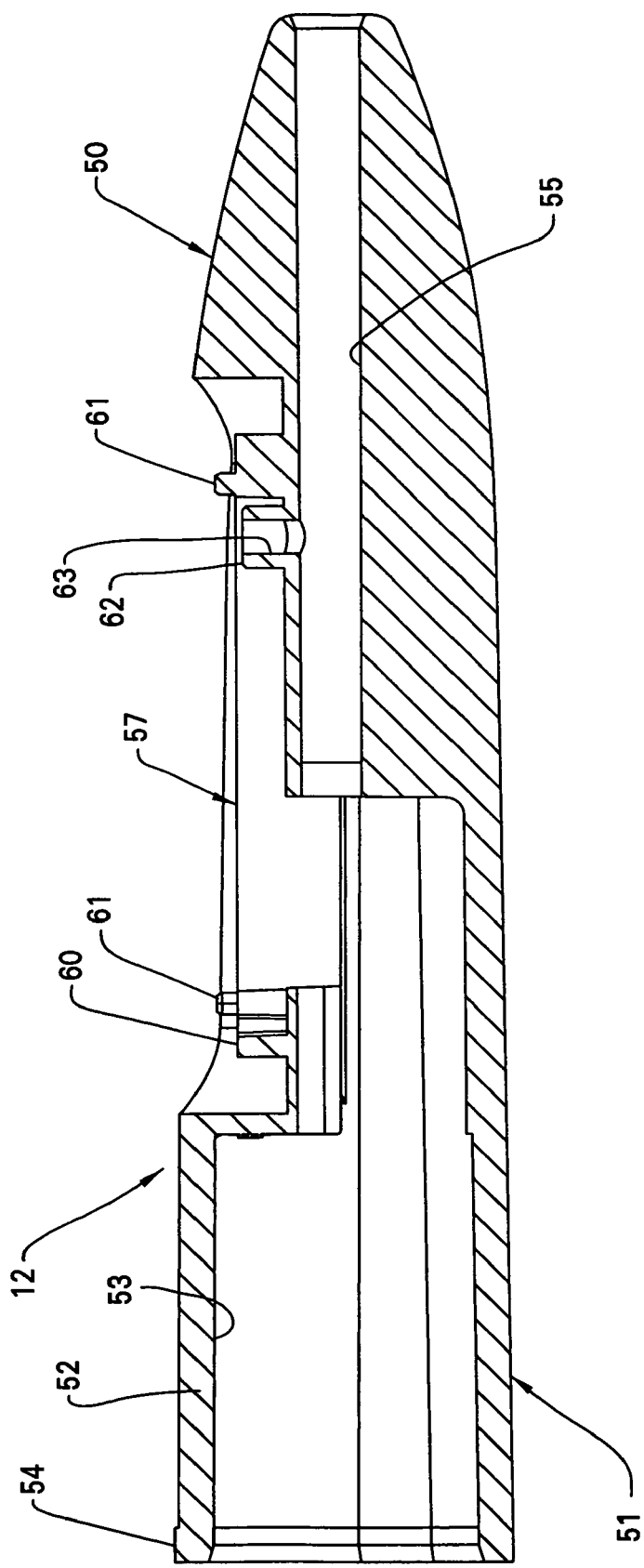
FIG. 3 is an enlarged longitudinal cross-sectional view of the nose-shaped member of the tool housing.

With reference to FIG. 3, nose-shaped member 12 is generally similar to nose-shaped member or nose cone disclosed in the '003 patent, and will also be only briefly described herein. Member 12 in the illustrated embodiment is constructed of rigid plastic, such as PVC or ABS. Member 12 is generally elongated in shape and includes a front end 50 having a tapered configuration, and a generally hollow rear end 51 which is joined to and projects rearwardly from front end 50. Rear end 51 is defined by a generally annular wall 52 which in turn defines a bore 53. Bore 53 opens rearwardly through a terminal distal edge 54 of rear end 51. Inner shell 29 of hub 13 is seated within the rearmost portion of bore 53 and engages edge 54. Front end 50 defines therein an elongate front bore 55 which opens through the distalmost end of front end 50 and extends rearwardly through front end 50 for communication with rear bore 53. Front bore 55 receives therein the proximal end of lumen assembly 14.

Member 12 additionally defines therein a wiring space 57 located in the upper portion of member 12, and which communicates with a forward portion of bore 53. A printed circuit board 58 is disposed in space 57, and wires 59 associated therewith extend downwardly into bore 53 for connection to respective socket crimps 38 disposed in hub 13, as discussed further below. Member 12 includes a generally upright flange 60 which is generally rectangularly-shaped for supporting circuit board 58. A pair of spaced-apart posts 61 are disposed within flange 60 to which the circuit board 58 is snap-fitted. A boss 62 is also provided within flange 60, and defines therein a conduit 63 which communicates with front bore 55. Conduit 63 may be utilized to inject adhesive into front bore 55 for securing lumen assembly 14 therein.

A web 64 is provided to cover the wiring space 57 and circuit board 58. Web 64 is includes two flexible buttons which define the moving components of switches 26 and 27 and are positioned over respective contact pads defined by circuit board 58. Circuit board 58 and web 64 are described in detail in the '003 patent, and are accordingly only briefly described above.

Turning now to lumen assembly 14, and with reference to FIGS. 6 and 7, assembly 14 is a four-tube structure which includes outer shaft 15 and insulating tube 16 (which is disposed over shaft 15), an elongate suction tube 73 formed from conductive material such as stainless steel, and a further insulating tube 74 disposed over suction tube 73. Similarly to insulating tube 16, insulating tube 74 in the illustrated embodiment is a heat-shrink tube. Outermost insulating tube 16 terminates distally of the terminal proximal end of outer shaft 15, and inner insulating tube 74 terminates distally of the terminal proximal end of suction tube 73.

Electrode 18 is provided at the distal end of outer shaft 15, and will be described herein with reference to FIGS. 7-9. Electrode 18 is constructed of conductive metal, such as a tungsten alloy, and in one embodiment may be formed by metal injection molding. Electrode 18 is generally tubular in shape and is defined by an annular wall which is separated into front and rear tubular and elongate wall portions 77 and 78 by a ring-shaped stop element 79 which projects transversely therefrom. A bore 84 of a constant diameter extends through portions 77 and 78. Stop element 79 defines therein a recess 80 which opens distally. The distal end of front wall portion 77 is closed off by an annular plate-like member 81 which is oriented at an angle relative to the central longitudinal axis of electrode 18. In one embodiment, the angle defined by plate-like member 81 and the electrode axis is approximately 60 degrees. Of course, this angular value is not intended to be limiting, and thus other angles would be within the scope of the invention. Plate-like member 81 defines therein a central opening 82 which is located inwardly of the annular periphery of member 81 and communicates with bore 84 of electrode 18. A plurality of projections 83 are cantilevered outwardly from the periphery of member 81. In the illustrated embodiment, projections 83 are uniformly disposed about the circumference of member 81 and are spaced radially outwardly from opening 82. Projections 83 define the tissue-working portions of electrode 18, and in this embodiment have generally rounded tips.

Electrode 18 is housed in a generally sleeve-shaped cap 86. Cap 86 is constructed of insulating material, such as ceramic. Cap 86 includes a proximal tubular portion 88 and a distally-oriented head 89 which extends from the distal end of tubular portion 88 and is enlarged in diameter relative thereto. In the illustrated embodiment, head 89 is generally wedge-shaped when viewed from the side or in longitudinal cross-section as in FIG. 7, and defines thereon a flat 90 which faces distally and extends arcuately over approximately half of the circumference of head 89. An outer surface 91 of head 89 is joined to a proximally-facing and generally upright shoulder 92, which shoulder 92 in turn is joined to an outer cylindrical surface 93 of proximal portion 88.

Cap 86 defines therein a main bore 95, and a counterbore 96 located proximally of and communicating with main bore 95. In forming counterbore 96, a portion of the material of cap 86 which defines main bore 95 remains so as to define a key 97 which projects longitudinally along cap 86 as well as radially inwardly, as best shown in FIG. 10. Bore 95 is sized to allow insertion of front portion 77 of electrode 18 therein, and counterbore 96 is sized so as to allow insertion of stop element 79 of electrode 18 therein. Further, key 97 is shaped so as to cooperate with recess 80 of electrode 18 as discussed below. A further counterbore 98 is located proximally of, communicates with, and is joined to counterbore 96 by a generally upright shoulder 99 which faces proximally. Counterbore 98 is sized so as to allow insertion of the distal ends of suction tube 73 and insulating tube 74 therein.

Electrode 18 according to the invention is secured to the conductive suction tube 73 by inserting the tubular rear portion 78 into the open distal end of suction tube 73. The stop element 79 of electrode 18 limits the extent to which electrode 18 can be inserted rearwardly into tube 73, and the terminal distal ends of tubes 73 and 74 accordingly abut, or are disposed immediately adjacent to, the proximally facing surface of stop element 79 when the electrode 18 is fully inserted, as shown in FIG. 7. The rear portion 78 of electrode 18 in the illustrated embodiment has an outer diameter which is sized similarly to the inner diameter of suction tube 73 to form a press or interference-fit between electrode 18 and suction tube 73. The proximal end of electrode 18 and the distal end of the suction tube 73 accordingly define respective connector elements which cooperate with one another to secure electrode 18 to suction tube 73. It will be appreciated that in addition to, or alternatively of, the above connection method, electrode 18 may be secured to suction tube 73 by other methods, such as by crimping or spot welding, or even conductive adhesive.

The insulating cap 86 is fitted over front portion 77 of electrode 18 by inserting portion 77 into main bore 95 of cap 86. Cap 86 is moved rearwardly relative to electrode 18 and tube 73 and during this movement, key 97 of cap 86 is circumferentially aligned with recess 80 of electrode 18 so as to correctly orient cap 86 relative thereto. Cap 86 is moved rearwardly until key 97 bottoms out in recess 80, which effectively seats stop element 79 of electrode 18 within counterbore 96, and positions the terminal ends of insulator tube 74 and suction tube 73 within counterbore 98 of cap 86. The distal end of electrode 18, including projections 83, projects distally beyond the head 89. The proximal end of suction tube 73 is inserted rearwardly into the open distal end 19 of outer shaft 15 (with insulating tube 16 mounted thereon) until the exposed distal end 19 of outer shaft 15 abuts shoulder 92 of cap 86. It will be appreciated that adhesive may be utilized to secure cap 86 to electrode 18, insulator tube 74, suction tube 73 and distal end 19 of outer shaft 15. The cap 86 serves to insulate the exposed distal end of the active electrode 18 from the return electrode defined by the distal end 19 of outer shaft 15.

Figure 5:
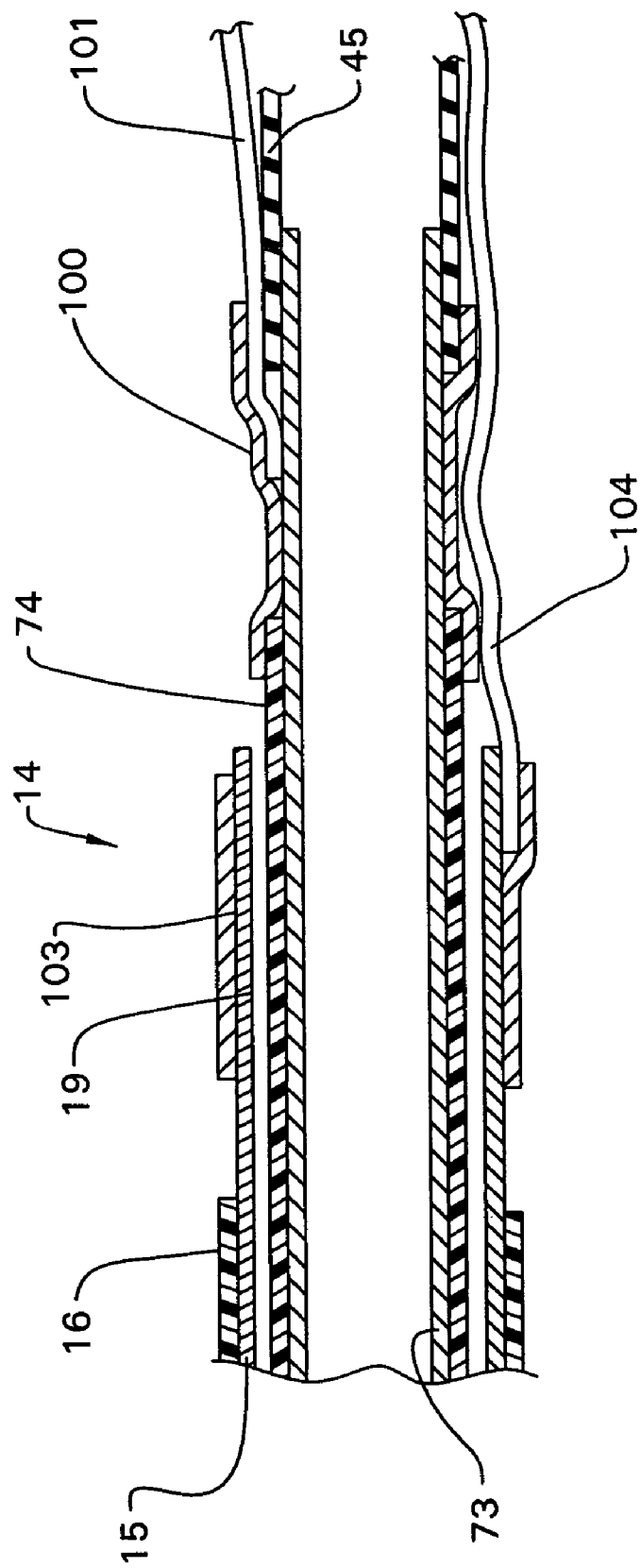
FIG. 5 is an enlarged, fragmentary longitudinal cross-sectional view of the proximal end of the lumen assembly which illustrates the wiring thereof.

With reference to FIGS. 4 and 5, the assembly of proximal end of lumen assembly 14 to rear hub 13 will now be described. In this regard, a heat-shrink band or solder band 100 is disposed about the exposed proximal end of suction tube 73 so as to electrically connect tube 73 to an active conductor wire 101. A further heat-shrink band or solder band 103 is disposed about the exposed proximal end 19 of outer shaft 15 so as to electrically connect shaft 15 to a return conductor wire 104. FIG. 4 illustrates bands 100 and 103 in a form prior to heat-shrinking, while FIG. 5 illustrates bands 100 and 103 subsequent to heat-shrinking. The end of suction tubing 45 disposed in opening 44 of hub 13 is fitted over the terminal proximal end of suction tube 73 prior to heat-shrinking band 100. It will be appreciated that the proximal end of lumen assembly 14, including shrunken band 103, is of a size so as to allow insertion of same into the rear open end of housing member 12 and forwardly into front bore 55 thereof. When inserted into bore 55, a forward portion of band 103 is located within bore 55, and the remainder of band 103 as well as band 100 are disposed in rear bore 53 of member 12 generally adjacent circuit board 58.

As shown in FIG. 4, in the illustrated embodiment, wires 101 and 104 are inserted into respective bores 36 defined in core 32 of hub 13, and are connected to distal ends 39 of respective socket crimps 58. Four wires 59 of circuit board 58 extending downwardly into rear bore 53 of member 12 are respectively inserted into the four remaining open bores 36 and are connected to distal ends 39 of the four remaining socket crimps 58. The opposite proximal ends 40 of socket crimps 58 receive respective pins (not shown) of cable connector 25.

Figure 11:
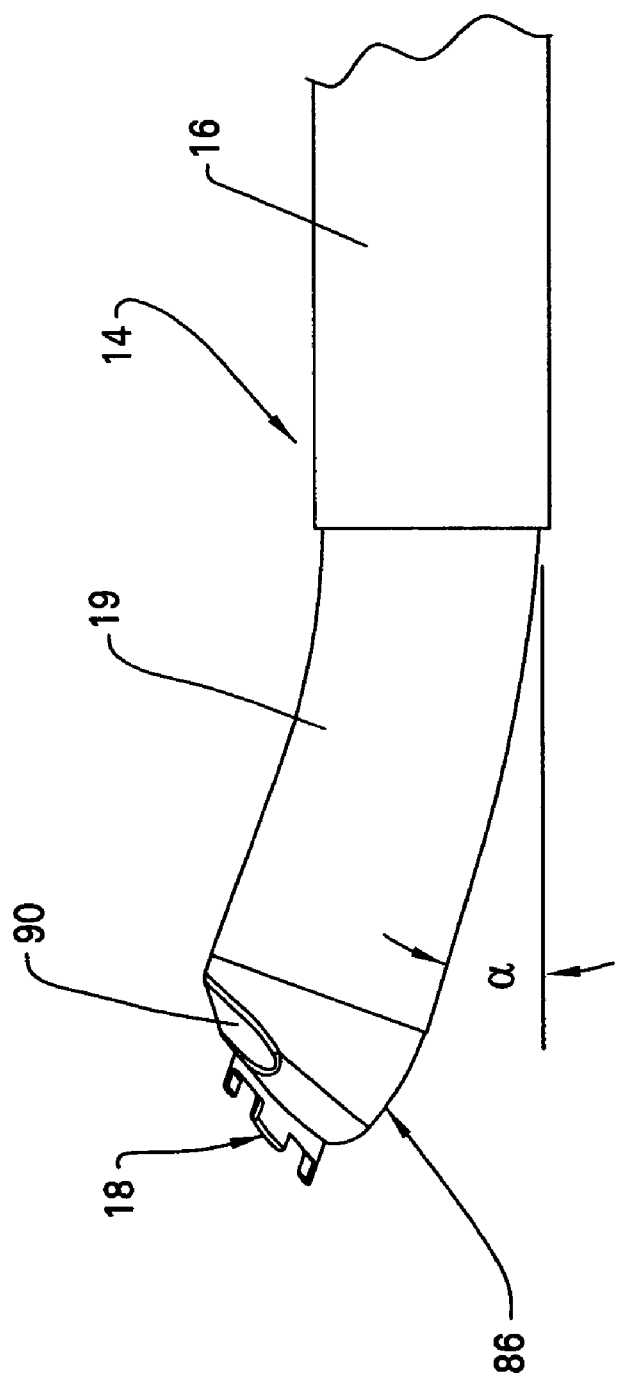
FIG. 11 is an enlarged, fragmentary side view of the lumen assembly in a bent configuration.

FIG. 11 illustrates the tool 10 having a distal end in a bent configuration, which in some surgical procedures is desirable to gain better access to targeted tissue at the surgical site. The tip of tool 10 in this embodiment is bent at an approximately 20 degree angle (alpha). When a bent tip is desirable or necessary, the flat 90 defined on the distal face of insulator 86 is designed to provide the surgeon with improved access to the surgical site.

The electrosurgical tool 10 is used to treat targeted tissue at the surgical site by energizing the tool 10 at the appropriate power level so as to either coagulate or ablate tissue as desired using the electrode 18. Suction is applied so as to remove fluid and other debris from the surgical site through opening 82 of electrode 18, through bore 84 thereof, through suction tube 73, and into and through suction tube 45 to the suction source.

Figure 13:
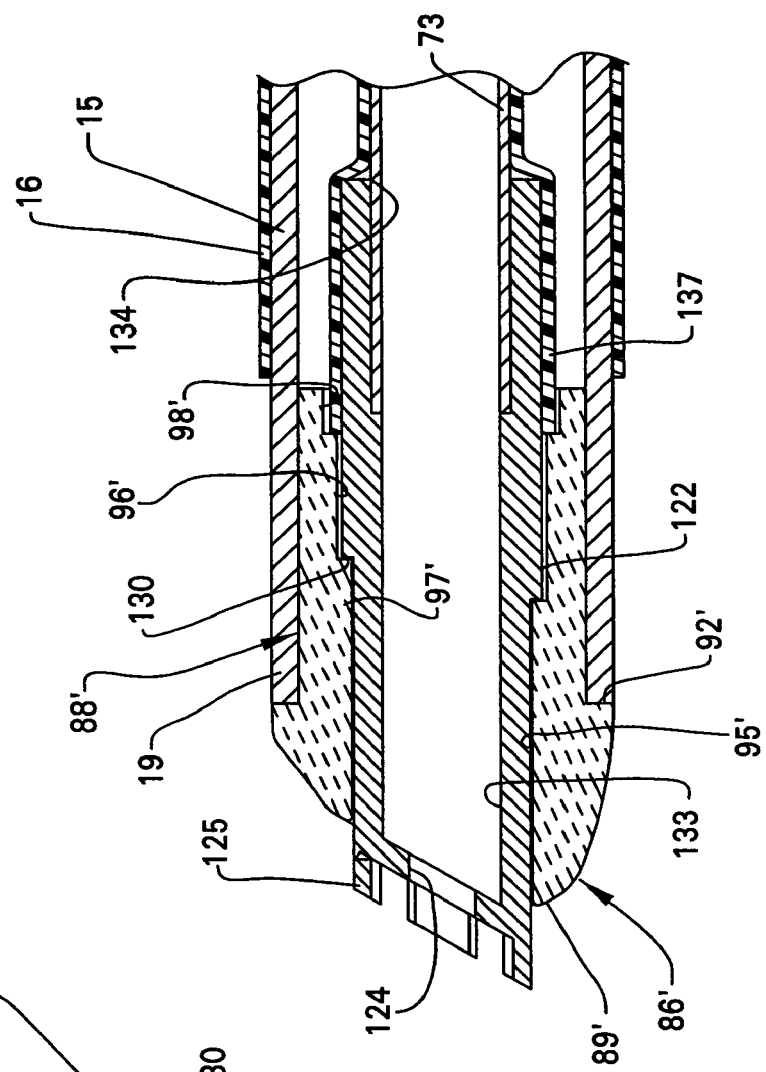
FIG. 13 is an enlarged, fragmentary longitudinal cross-sectional view of the assembled electrode of FIG. 12 and insulating cap.
Figure 12:
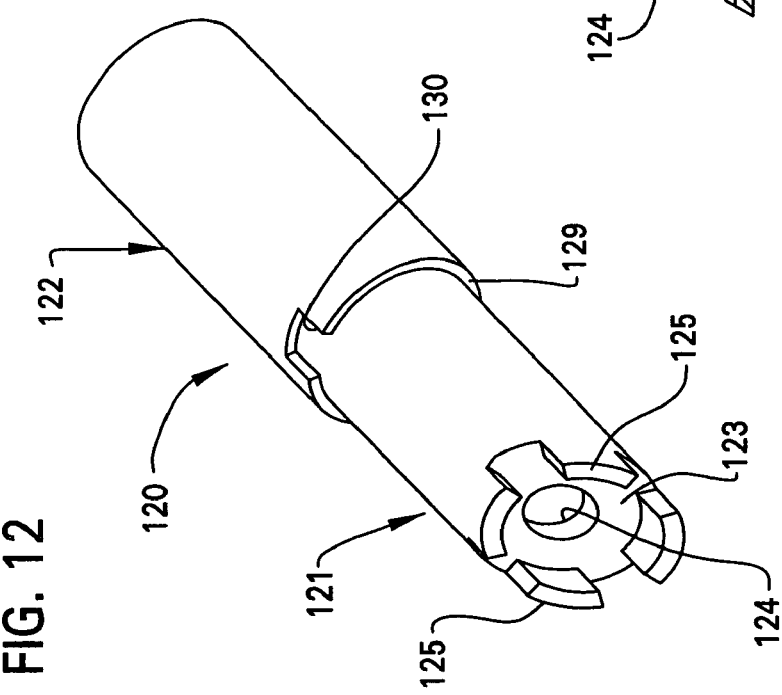
FIG. 12 is an enlarged, perspective view of a further embodiment of an active electrode.

FIGS. 12 and 13 illustrate a further embodiment of an electrode 120 according to the invention, which electrode 120 is configured to accept the distal end of the suction tube 73 therein. Electrode 120 is generally tubular in shape and is defined by front and rear tubular portions 121 and 122. The distal end of front portion 121 is closed off by a plate-like member 123 oriented at an angle relative to the central longitudinal axis of electrode 120, as in the first embodiment. Member 123 defines therein a central suction opening 124 located inwardly of the periphery of member 123 and communicates with the interior of electrode 120. A plurality of projections 125 are cantilevered outwardly from the periphery of plate-like member 123, and are uniformly disposed about the circumference thereof. In this embodiment, projections 125, which define the tissue-working portions of electrode 120, define sharp edges at their distalmost ends, as compared to the rounded configuration of projections 83 discussed above. However, it will be appreciated that the projections 125 may alternatively be rounded, and also that both projections 83 and 125 may have other configurations that than disclosed herein depending upon the requirements of the particular surgery during which the tool is to be utilized.

Rear portion 122 of electrode 120 is of a larger outer diameter than front portion 121, and a shoulder 129 is defined at the transition between front and rear portions 121 and 122. A recess 130 projects rearwardly from shoulder 129 and opens distally. Electrode 120 defines therein a bore 133 which extends rearwardly from the plate-like member 123, through front portion 121, and approximately part-way through rear portion 122. A counterbore 134 communicates with bore 133 and opens rearwardly through the proximal end of rear portion 122. In this embodiment, counterbore 134 is sized so as to receive the distal end of suction tube 73 therein.

Electrode 120 is disposed within a sleeve-shaped insulating cap 86', which is substantially identical in configuration to cap 86 discussed above. The same reference numbers, plus a prime, are accordingly utilized to reference various structures of cap 86'. In this embodiment, bore 95' of cap 86' is sized to receive front portion 121 of electrode 120, counterbore 96' is sized to receive the front end of rear portion 122, and key 97' is sized to cooperate with recess 130.

Electrode 120 is secured to the suction tube 73 by inserting the distal end of suction tube 73 into counterbore 134. The diameter of counterbore 134 is accordingly sized similarly to the outer diameter of suction tube 73 to form a press or interference-fit between electrode 120 and suction tube 73. As in the prior embodiment, the electrode 120 may alternatively or additionally be secured to suction tube 73 by crimping, welding, a conductive adhesive or other suitable fastening arrangement. In order to electrically insulate the proximal end of electrode 120 and suction tube 73 from the conductive outer shaft 15, an insulating material, such as a heat-shrink insulating tube 137 (similar to tube 74 described above) is applied over the majority of the length of the suction tube 73 and over the intersection between suction tube 73 and the proximal end of rear portion 122 of electrode 120, as shown in FIG. 13.

The insulating cap 86' is fitted over the front portion 121 of electrode 120 in a similar manner as discussed above. That is, front portion 121 of electrode 120 is inserted into main bore 95' of cap 86'. Cap 86' is moved rearwardly relative to electrode 120, and key 97' of cap 86' is aligned with recess 130. Cap 86' is moved rearwardly until key 97' bottoms out in recess 130, which effectively seats the distal end of insulating tube 137 within counterbore 98'. The proximal end of suction tube 73 is inserted rearwardly into the open distal end 19 of outer shaft 15, until the end 19 of outer shaft abuts shoulder 92' of cap 86'. Adhesive may be utilized to secure cap 86' to electrode 120, insulator tube 137, and distal end 19 of outer shaft 15. The proximal end of the above assembly is then assembled to hub 13 as in the first embodiment.

As in the prior embodiment, the proximal end of electrode 120 and the distal end of suction tube 73 define respective connectors which cooperate with one another to firmly secure electrode 120 to suction tube 73.

FIGS. 14-18 illustrate a further embodiment of an electrode arrangement 161 according to the invention. The electrode arrangement 161 in this embodiment is utilized when it is desirable to treat large sections of body tissue, such as in shoulder surgery wherein large amounts of tissue must be removed in order to expose bone.

Electrode arrangement 161 includes an active electrode 162 having a front portion 163 and a rear mounting portion 164, which are oriented transversely relative to one another, and in the illustrated embodiment are oriented at a 90 degree angle. Front portion 163 is defined by a ring-like wall 165 which includes a downwardly opening lower part 166 joined to mounting portion 164. Mounting portion 164 projects sidewardly or rearwardly from lower part 166. Rear mounting portion 164 is generally cylindrical in shape and defines a bore 167 therein which opens rearwardly. The outer diameter of portion 164 is sized similarly to the inner diameter of suction tube 73.

Wall 165 additionally includes an upper part 171 which defines the tissue-working portion of electrode 162. Upper part 171 includes a plurality of generally post-shaped projections 172 oriented in a generally upright manner. In the illustrated embodiment, the projections 172 are joined to one another by arcuate wall sections 173, each of which extends between two adjacent projections 172. A plate-like member 174 closes off the upper end of front portion 163, and defines a pair of axially-spaced suction openings 178 therein which communicate with the hollow interior of electrode 162 and suction tube 73. A step 180 defines the intersection between upper part 171 and lower part 166. The outer peripheral edge of step 180 defines the outer lateral perimeter of electrode 162, and wall sections 173 are disposed horizontally inwardly from this outer perimeter.

Figure 17:
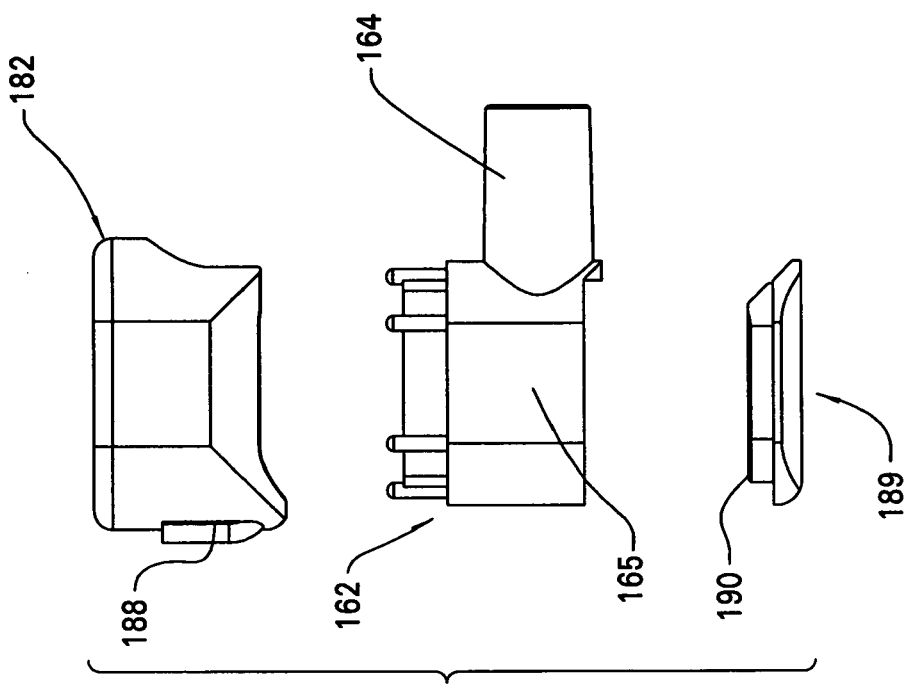
FIG. 17 is an enlarged exploded side view of the electrode, base and cap of the FIG. 14 electrode arrangement.
Figure 16:
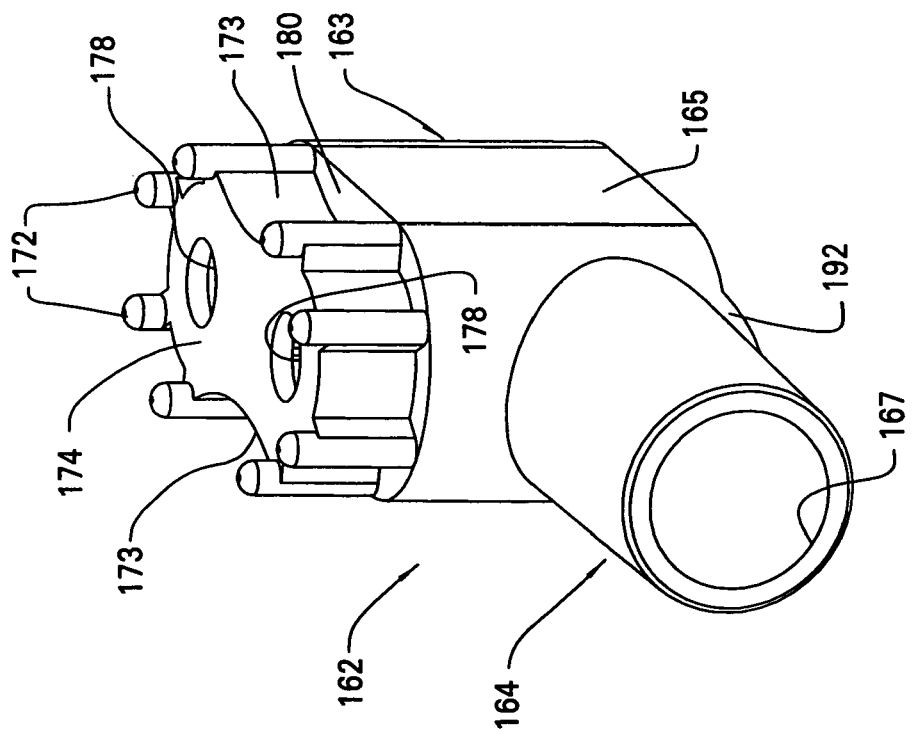
FIG. 16 is an enlarged perspective view of the electrode of the FIG. 14 electrode arrangement in isolation.
Figure 18:
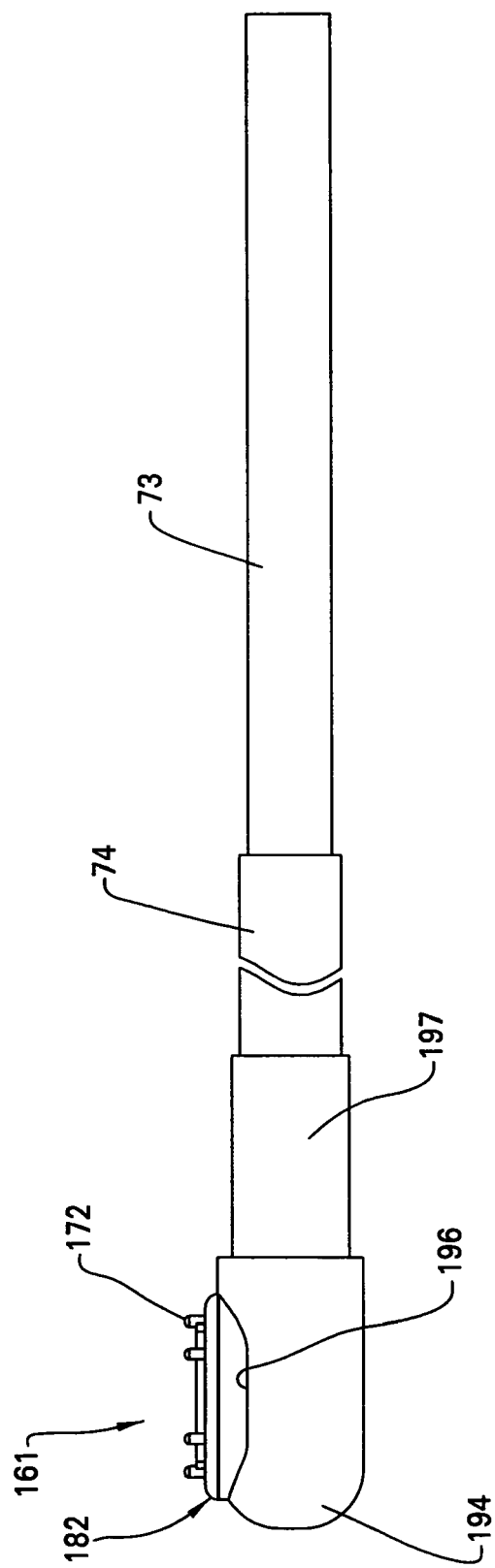
FIG. 18 is an enlarged, fragmentary side view of the FIG. 14 electrode arrangement.

An insulating cap 182, shown in isolation in FIG. 17, is disposed over front portion 163 of electrode 162. Insulating cap 182 is defined by a generally upright wall 183 which opens both rearwardly and downwardly, and conforms to the outer surface configuration of electrode 162. Insulating cap 182 additionally defines thereon a generally horizontally oriented upper annular flange 187 which projects inwardly from an upper edge of wall 183, and a rib-like projection 188 which projects rearwardly from wall 183. Electrode arrangement 161 also includes a base 189 including an upwardly projecting mounting flange 190 and a proximally-opening recess 191.

Electrode 162 and base 189 are constructed, for example, of a tungsten alloy. Other suitable materials would be within the scope of the invention. Insulating cap 182 may be constructed of plastic, and may be formed by injection molding or overmolding.

Electrode 162 is assembled to base 189 by inserting base 189 into the lower open end thereof, so that flange 190 of base 189 is positioned against the lower inner surface of wall 165 and so that a lower flange 192 of mounting portion 164 seats in recess 191. Mounting portion 164 of electrode 162 is then inserted into the open distal ends of suction tube 73 and insulator tube 74, until the distal ends of tube 73 and insulator 74 are disposed immediately adjacent or abut the outer surface of wall 165 located around the base of mounting portion 164. Cap 182 is then fitted over front portion 163 of electrode 162, and secured with adhesive. Adhesive may also be used to fill any gaps between cap 182 and electrode 162. The distal end of the above assembly is then provided with a head member 194, for example by overmolding, which completely covers the distal end of the assembly, except for the upper face or working portion of electrode 162. Head 194 is constructed of an insulating plastic material, and includes a front cap 195 defining an opening 196 through which the uppermost portions of electrode 162 and insulating cap 182 project. Head 194 additionally includes a rearwardly projecting sleeve 197 disposed in surrounding relation with the distal end of suction tube 73, insulating tube 74, and part of rear mounting portion 164. The distal end of sleeve 197 adjoins the proximal end of front cap 195 at an annular shoulder 199 which faces rearwardly. The sleeve 197 is then inserted into the open distal end 19 of outer shaft 15, until shaft end 19 abuts shoulder 199. The outer diameter of sleeve 197 is accordingly similar in dimension to the inner diameter of outer shaft 15 to provide a snug fit, and the two components may additionally be secured with adhesive.

As discussed above, the electrode arrangement 161 is intended for use during surgical procedures which require removal of large volumes of tissue. The arrangement 161 is therefore larger in overall size than the above electrode arrangements. Further, the pair of suction openings 178 provided at the distal end of the tool permit removal of large amounts of fluid and/or surgical debris.

As will be appreciated from the above description, the embodiments according to the invention provide an electrically-conductive suction tube and a modular electrode which is initially separate from the suction tube, and then secured to the distal end of the suction tube. The above arrangement allows the electrode to be configured in a way which will achieve high-density current delivery to targeted tissue, resulting in rapid tissue treatment. Further, the invention provides the ability to reduce the overall size of the tool, by eliminating the need for electrical wiring to extend through the length of the lumen assembly, and also by integrating the functions of energy delivery and suction into one component, i.e. the suction tube.

Although a particular preferred embodiment of the invention has been disclosed in detail for illustrative purposes, it will be recognized that variations or modifications of the disclosed apparatus, including the rearrangement of parts, lie within the scope of the present invention.

What is claimed is:

1. An electrosurgical tool comprising:
a housing disposed at and defining a proximal end of said tool; and
a lumen assembly projecting from a distal end of said housing and including an elongated outer shaft defining a hollow interior, a distal end of said outer shaft comprising an electrically conductive material and defining a return electrode, a suction conduit defined within said outer shaft and in communication with a suction source, a suction tube disposed within said hollow interior of said outer shaft and defining a conduit therein forming part of said suction conduit, said suction tube comprising an electrically conductive material and being connected to a source of electrical energy, an electrode element comprising an electrically conductive material and having a distal end defining an active, energy-delivering electrode at a distal end of said lumen assembly and an electrically conductive proximal end, and an insulator disposed between said return electrode and said active electrode, said proximal end of said electrode element and an electrically conductive distal end of said suction tube defining respective connectors which cooperate to define a connection area directly between said electrode element and said suction tube, said connection area electrically connecting said electrode element to said suction tube such that said suction tube delivers electrical energy to said active electrode.

2. The tool of claim 1, wherein said electrode element defines a hollow interior which communicates with said conduit of said suction tube, and said distal end of said electrode element defines an opening therein which opens into said hollow interior of said electrode element and defines a suction opening, said suction opening and said hollow interior of said electrode element both forming part of said suction conduit of said lumen assembly.

3. The tool of claim 1, wherein said connection area comprises an interference-fit.

4. The tool of claim 1, wherein said connectors are both tubular in configuration, and one of said connectors is press-fit into the other said connector.

5. The tool of claim 1, wherein said electrode element defines a suction opening which communicates with said conduit of said suction tube, said suction opening being disposed distally of said distal end of said suction tube and forming part of said suction conduit of said lumen assembly.

6. The tool of claim 5, wherein said active electrode defines thereon a tissue contacting portion which delivers electrical energy to targeted tissue, and said suction opening is spaced from said tissue contacting portion.

7. The tool of claim 5, wherein said electrode element is tubular in configuration, and said active electrode defines thereon a tissue contacting portion arranged generally annularly along a periphery thereof, and said suction opening is spaced radially inwardly from said tissue contacting portion.

8. The tool of claim 1, wherein said electrode element is fixedly secured to said suction tube at said connection area, but is initially a separate component from said suction tube.

9. The tool of claim 1, wherein said insulator is annular in configuration and is disposed in surrounding relation with said electrode element, a proximal portion of said insulator being disposed within said distal end of said outer shaft.

10. The tool of claim 9, wherein a first insulating tube is disposed between an outer surface of said suction tube and an inner surface of said outer shaft, and a second insulating tube is disposed about an outer surface of said outer shaft, said distal end of said outer shaft being exposed from said second insulating tube so as to define said return electrode.

11. The tool of claim 1, wherein said connectors are both tubular in configuration, and said connector of said electrode element is disposed within an interior of said connector of said suction tube.

12. The tool of claim 1, wherein said connectors are both tubular in configuration, and said connector of said suction tube is disposed within an interior of said connector of said electrode element.

13. The tool of claim 1, wherein said suction tube is constructed entirely of said conductive material, and said tool further includes a suction supply tube connected to a proximal end of said suction tube disposed adjacent said housing.

14. The tool of claim 1, wherein said active electrode is disposed transversely relative to a longitudinal axis of said suction tube.

15. The tool of claim 1, wherein said electrode element defines a passage therein, said passage being enclosed within said electrode element by an outer wall of said electrode element, said passage communicating with said conduit of said suction tube and defining part of said suction conduit of said lumen assembly.

16. The tool of claim 1, wherein said insulator is annular in shape and is disposed in surrounding relation with said distal end of said electrode element, said insulator defining a single opening therethrough in which said electrode element is disposed.

17. The tool of claim 1, wherein each said connector is tubular in configuration and includes an outer wall having an interior surface which defines a conduit within said connector, said connectors being disposed in telescoping relation with one another, said electrode element defining a suction opening adjacent said distal end thereof, said conduit of the innermost one of said connectors and said suction opening each communicating with said conduit of said suction tube and defining part of said suction conduit of said lumen assembly.

18. An electrosurgical tool comprising a handle defining a proximal end portion of said tool, an elongate tubular shaft projecting from said handle and comprising a conductive material, said shaft having a conductive tubular distal end and defining a suction conduit therein in communication with a suction source to permit suction to be drawn through and along said shaft through a suction opening defined at a distal end of said tool, and a tubular electrode element comprising a conductive material and having a conductive tubular proximal end, one of said conductive tubular ends being disposed within the other said conductive tubular end, said electrode element having a distal end defining an active, energy-delivering electrode for treating tissue, said shaft being connected to a source of electrical energy and said conductive tubular end of said shaft being disposed in direct electrical contact with said conductive tubular end of said electrode element such that said shaft defines an electrical energy-delivering pathway along said tool to said active electrode.

19. The tool of claim 18, wherein said shaft is an inner shaft and said tool includes an elongate outer shaft defining a hollow interior in which said inner shaft is disposed.

20. The tool of claim 19, wherein said outer shaft includes a distal end disposed adjacent said active electrode, said distal end defining a return electrode, and said tool including an insulator disposed between said active and return electrodes.

21. The tool of claim 18, wherein said tubular ends of said electrode element and said shaft together define a connection area between said shaft and said electrode element, said connection area comprising an interference-fit.

22. The tool of claim 18, wherein said tubular end of said electrode element is disposed coaxially within said tubular end of said shaft.

23. The tool of claim 18, wherein said tubular end of said shaft is disposed coaxially within said tubular end of said electrode element.

24. The tool of claim 18, wherein said distal end of said electrode element defines said suction opening therein.

25. The tool of claim 24, wherein said electrode element defines a conduit therein which communicates with said shaft conduit such that suction is drawn from a surgical site through said suction opening, through said electrode element, and through said shaft to a source of suction.

26. The tool of claim 18, wherein said shaft has an inner surface which defines said conduit.

27. The tool of claim 18, wherein said tubular end of said electrode element is defined by a continuous wall which encloses a passage therein.

28. The tool of claim 18, wherein said tubular ends together define a connection area between said shaft and said electrode element, said one tubular end disposed innermost at said connection area being defined by a continuous wall which defines a suction passage enclosed by said wall, said suction passage communicating with said suction conduit and the suction source to permit suction through said connection area.

29. A method of assembling an electrosurgical tool including a handle defining a proximal end portion of the tool, an elongate, electrically-conductive tubular shaft projecting from the handle and defining a suction conduit therein in communication with a suction source to permit suction to be drawn through and along the shaft through a suction opening defined at a distal end of the tool, the shaft having a conductive tubular distal end, and an electrically-conductive electrode element having a distal end defining an active, energy-delivering electrode for treating tissue and a conductive tubular proximal end, said method comprising the steps of:

inserting one of the tubular ends into the other of the tubular ends to interconnect the electrode element and the shaft so that the conductive tubular end of the shaft is disposed in direct electrical contact with the conductive tubular end of the electrode element; and connecting the shaft to a source of electrical energy such that the shaft defines an electrical energy-delivering pathway along said tool to the active electrode.

30. The method of claim 29, wherein said step of inserting comprises press-fitting one of the tubular ends into the other of the tubular ends.

* * * * *